United States Patent [19]

Rose

[11] Patent Number: 4,846,199

[45] Date of Patent: Jul. 11, 1989

[54] SMOKING OF REGENERATED TOBACCO SMOKE

[75] Inventor: Jed E. Rose, Venice, Calif.

[73] Assignee: The Regents of the University of California, Berkley, Calif.

[21] Appl. No.: 840,072

[22] Filed: Mar. 17, 1986

[51] Int. Cl.$^4$ .............. A24B 3/18; A24B 15/18; A24F 1/00; A24D 1/00

[52] U.S. Cl. .................. 131/329; 131/270; 131/273; 131/198.2; 131/360; 131/290

[58] Field of Search ........... 131/329, 270, 273, 198.1, 131/198.2, 202, 201, 360, 359, 290

[56] References Cited

U.S. PATENT DOCUMENTS 1,535,934 4/1925 McFadden ............ 131/201
3,397,703 8/1968 Otto ..................... 131/201
4,474,191 10/1984 Steiner ................. 131/198.2

Primary Examiner—V. Millin
Attorney, Agent, or Firm—Robert J. Schaap

[57] ABSTRACT

A method and an apparatus for regenerating tobacco smoke separation of the gaseous constituents from the condensed constituents. The gaseous constituents which contain many of the harmful substances in tobacco smoke are eliminated and the residue of the condensed constituents is collected. For purposes of smoking the condensate, an aerosol is produced from this condensate for inhalation by the smoker. Heating is an effective means to produce the aerosol and since the heating occurs at low temperature, there is no re-combustion of tobacco and the attendant production of harmful constituents.

43 Claims, 3 Drawing Sheets

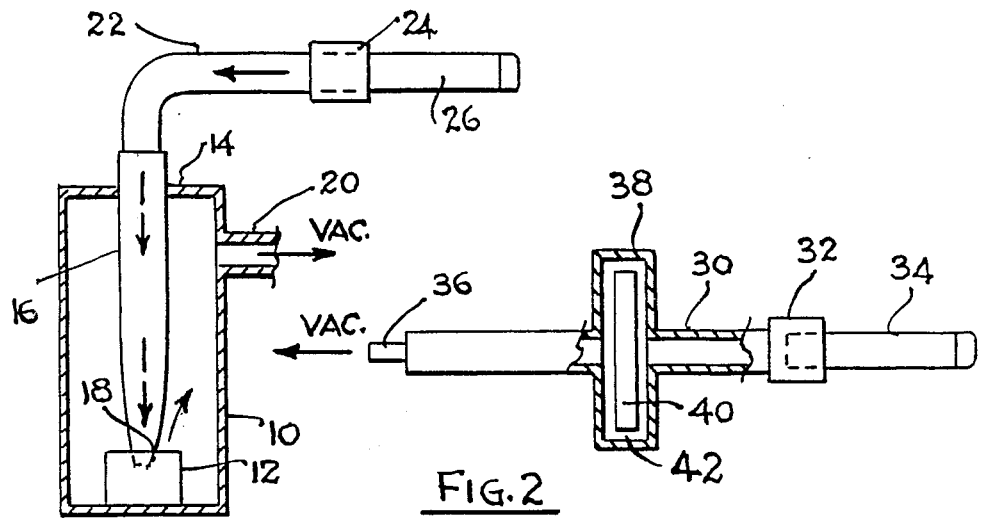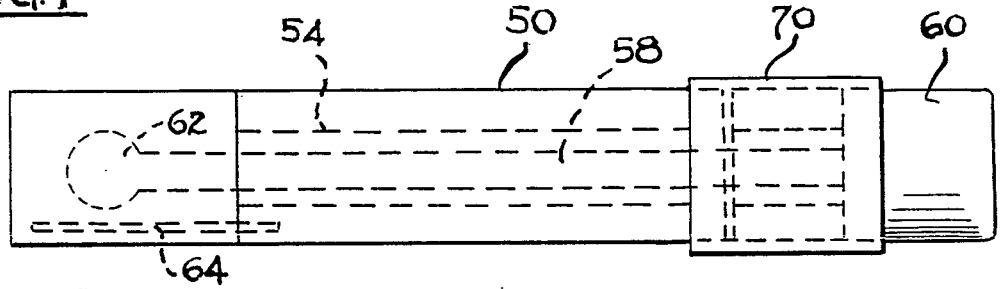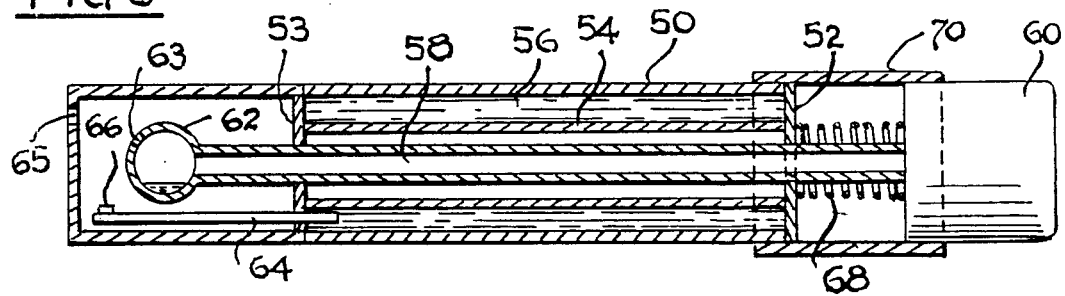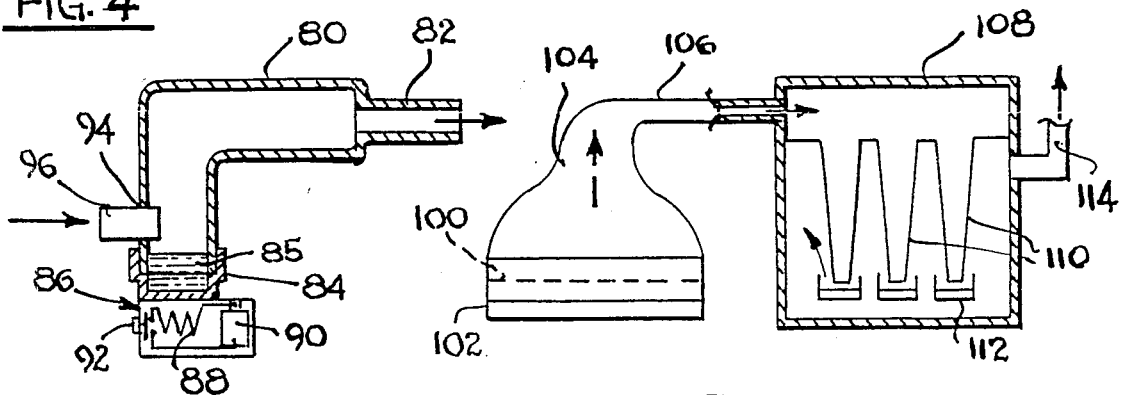

SMOKING OF REGENERATED TOBACCO SMOKE

GOVERNMENT RIGHTS

This invention was made with U.S. Government support under Grant No. NIDA DA02665 awarded by the Department of Health and Human Services; also with the material support of the Veterans Administration. The Government has certain rights in this invention.

BACKGROUND OF THE INVENTION

1. Field of the Invention

This invention relates in general to certain new and useful improvements in apparatus and method for enabling smoking tobacco and other burnable plant substances with substantially reduced health hazards and more particularly to an apparatus and method which uses regenerated tobacco smoke without many of the highly toxic gaseous constituents normally present in tobacco smoke.

2. Brief Description of the Prior Art

In recent years, with the recognition of the harmful effects of tobacco smoking, there have been numerous campaigns and programs by governmental agencies and various health groups and other interested organizations to disseminate information about the adverse health effects resulting from tobacco smoking. Moreover, and as a result of this recognition of the harmful effects, there have been many programs directed to attempts to reduce smoking incidence.

The present successes in achieving reduction in the incidence of smoking have been relatively poor with presently known techniques. The present state of the art involves both behavioral approaches and pharmacological approaches. Approximately 80% or more of the tobacco smokers who initially quit smoking after using some behavioral or pharmacological approach to singly reduce smoking incidence, generally relapse and return to the habit of smoking at their former rate of smoking within about a one year period of time.

The behaviorial and psychological approach primarily relies upon behavior modification. There have been several programs which employ reward and punishment techniques to reduce the desire for smoking. However, as indicated above, these approaches have not proved to be very effective.

Another commonly employed approach to reduce the incidence of tobacco smoking relies on substitute smoking devices. The so-called "low tar and nicotine" cigarette has been offered as a means of providing a safer mode of smoking. However, these cigarettes often suffer from the lack of taste to which the normal smoker is accustomed and notwithstanding, these cigarettes do not eliminate or even reduce many of the harmful gases present in cigarette smoke.

One of the most successful approaches to date in reducing the incidence of smoking relies upon nicotine containing chewing gum which is designed to reduce smoking withdrawal symptoms. The use of the nicotine gum suffers from several problems including not only the bad taste and destruction of dental appliances, but the gastrointestinal upset which results therefrom and which also reduces compliance. In addition, it has been found that the nicotine containing gum does not satisfy the craving that most smokers experience for the distinct sensations in the throat and chest elicited by nicotine in the smoke. Over the course of many years of tobacco smoking, these particular sensations have become an important part of and associated with the habit of smokers and give rise to tobacco smoke dependency in most of the tobacco smokers.

In view of the fact that the presently available techniques and substitutes for smoking have not significantly reduced the number of smokers or at least aided in reducing the incidence of smoking in any particular smoker, recent attention has been directed to finding some substitute which will satisfy the craving of the smoker but which eliminates many of the harmful side effects of smoking. It is also desirable to provide such a substitute which will also have some effect in reducing the incidence of smoking.

There has been recent attention directed to the modification of either the tobacco or of the cigarette in order to reduce some of the direct harmful effects of cigarette smoking, but which will still provide the desired sensory effects. One of the common techniques employed is that of the adding of a filter to the cigarette which serves the function of diluting the smoke stream and blocks some of the harmful particulate material, such as several harmful tars and the like. To some extent the filter also blocks some of the gaseous constitutents. The filtered cigarette has met with a fairly substantial amount of success, although it only has limited effectiveness in reducing the direct harmful effects of tobacco smoke. For example, the filter does not remove many or otherwise substantial quantities of the quite harmful and generally poisonous gases, such as hydrogen cyanide, carbon monoxide, ammonia and formaldehyde which are generated in cigarette smoke.

There has also been some attempt to breed tobacco plants with less carcinogenic constituents. However, this approach has also met with limited success. At present there is insufficient technology or knowledge to selectively and efficiently breed the tobacco without the harmful constituents. Notwithstanding, even with the genetic breeding of tobacco plants, there will always be the inherent generation of some of the harmful gases such as carbon monoxide and possibly hydrogen cyanide upon combustion of tobacco leaves.

There is a non-combustible cigarette which delivers nicotine vapors presently under development. It was theorized that the delivery of nicotine and a sustaining of a certain level of nicotine in the blood stream of the individual would satisfy the nicotine craving of the smoker. However, this proposed nicotine vapor cigarette has many shortcomings in that the vapor delivery system does not deliver nicotine to the same region of the respiratory tract as an aerosol such as the cigarette smoke. As a result, there is an excess of taste of nicotine in the mouth which is quite undesirable. The aroma also differs substantially from that of a conventional cigarette. Even more importantly, the amount of nicotine delivered is substantially less than many commercial cigarette brands would deliver and thus, does not satisfy the nicotine craving of the smoker. In effect, there has not been any effective means to enable a tobacco smoker to continue with the smoking habit and receive the same sensory pleasure to which the smoker was normally accustomed and with the elimination of many of the harmful constitutes present in the tobacco smoke.

OBJECTS OF THE INVENTION

It is, therefore, one of the primary objects of the present invention to provide a method of regenerating tobacco smoke and which is capable of being smoked without many of the harmful substances normally present in tobacco smoke.

It is another object of the present invention to provide a method of regenerating a tobacco smoke by separating the harmful gaseous components from the particulate condensates and which condensates are capable of being smoked upon forming an aerosol therewith.

It is a further object of the present invention to provide an apparatus for producing tobacco smoke and which provides for the separation of the gaseous constituents from the fluidized constituents in tobacco smoke upon combustion thereof and also provides for collecting the fluidized constituents for later forming an aerosol thereof.

It is an additional object of the present invention to provide a method of smoking constituents of tobacco smoke with the same sensory effects normally provided by tobacco smoke but without many of the harmful constituents normally included in tobacco smoke.

It is another salient object of the present invention to provide a two step process of combusting tobacco smoke and collecting certain constituents thereof and thereafter smoking an aerosol containing such constituents.

It is still another object of the present invention to provide a method for reducing the incidence of tobacco smoking by providing a tobacco smoke substitute.

With the above and other objects in view, my invention resides in the novel features of form, construction, arrangement and combination of steps in the method and apparatus hereinafter described.

BRIEF SUMMARY OF THE DISCLOSURE

This invention relates in a broad aspect to a method and apparatus for providing a substitute for normal tobacco smoke as well as a method for reducing the incidence of tobacco smoking.

The present invention is primarily concerned with the smoking of condensates of combusted tobacco smoke. It is well established that tobacco smoke and smoke from other plant substances contain a large number of gaseous constituents, many of which are poisonous.

The gaseous constituents in tobacco smoke, contain for example, hydrogen cyanide, ammonia, formaldehyde in a gaseous phase, carbon monoxide and the less harmful carbon dioxide. Water vapor, nitrogen and oxygen are usually also present in the gaseous constituents. Inasmuch as many of these gaseous constituents are highly poisonous, it is desirable to eliminate them from the normal tobacco smoke.

The normal tobacco smoke also contains the condensates which constitute the visible part of the smoke stream. These condensates are typically comprised of small solid particles and liquid particles or droplets. Inasmuch as the condensates are present in normal tobacco smoke and operate to form a vapor stream (even though not in a gaseous state), they are often times referred to as "fluidized" constituents. Nevertheless, after the tobacco has been ignited and combusted, after a short period of time, the solid and liquid particles do condense to form the condensate. This condensate is usually composed of several tar-like substances.

In accordance with the present invention, these condensed tars are used to generate an aerosol which is capable of being inhaled. This aerosol contains many of the particles normally generated in the tobacco smoke and thus, satisfies most of the desired sensory effects which are achieved with normal tobacco smoke and without the harmful gaseous ingredients contained therein. Thus, when the aerosol is generated, it may be inhaled in the same manner as normal tobacco smoke.

The term "smoking" is used to refer to the inhalation or the drawing of the aerosol which is generated, although it should be understood that in a strict sense, the aerosol is not smoke, as such, from a combusted tobacco.

In one aspect, the present invention includes a method of producing tobacco smoke residue which is capable of being smoked. Any method of generating a residue of the condensed constituents, or particulate constitutents, and separation of the gaseous constitutents may be employed. For example, one method of generating the tobacco smoke residue is by a selective distillation of tobacco leaves. Other anaerobic techniques may be employed.

In a preferred embodiment of the invention, the method of producing tobacco smoke comprises the burning of the tobacco to produce a smoke which is comprised of fluidized components or constituents, i.e. the condensed constituents, and the gaseous components or constituents. Thereafter, the gaseous constituents are separated from the fluidized constituents and the gaseous constituents are discharged since they contain many of the harmful substances normally present in tobacco smoke. The condensed constituents or so-called "condensates" are collected for smoking upon generation of an aerosol of these condensates.

In one embodiment of the invention, the gaseous constituents are separated from the condensed constituents by use of a filter which causes a separation of the condensed constituents at the filter by interruption by filter fibers, while allowing many of the gaseous constitutents to pass through the filter for removal thereof. In another embodiment of the present invention, the gaseous constituents are separated from the condensed constituents by passing the tobacco smoke through a tapered tube which causes a progressive and substantial increase in the velocity of the smoke stream as it passes through the tube. Thereafter, the mixture of the gaseous constituents and condensed constituents in the smoke stream suffers a directional change at a very sharp angle thereby causing the condensed constituents to effectively precipitate from the gaseous constituents. In a more preferred embodiment, this tube is a Pasteur pipette.

The present invention also provides an apparatus for producing tobacco smoke residue which is capable of being smoked when an aerosol of that residue is generated, as for example, upon heating of the residue (condensed constituents) in the presence of air. This apparatus comprises a means for receiving a source of tobacco which is capable of being combusted to produce the tobacco smoke. A chamber temporarily receives and holds the tobacco smoke. A separating mechanism is operatively connected to this chamber to receive the tobacco smoke and separates the gaseous constituents in the smoke from the condensed constituents. An exhaust member is provided for discharging the gaseous constituents which have been separated and a container is provided for collecting the condensed constituents.

In still another aspect, the present invention comprises a method of smoking reconstituted tobacco smoke to provide the sensory effects of normal tobacco smoke without many of the harmful gaseous constituents therein. This method comprises disposing a container of the condensed components separated from tobacco smoke in relationship to a source of heat. Thereafter, the container is heated to generate a vapor of the condensed constituents when the user thereof desires to inhale smoke. The vapor is passed through a smoke delivery tube upon drawing thereof by a smoker to allow receipt in the oral cavity and respiratory tract of the smoker.

In one embodiment, this latter method comprises the locating of the container where it is not heated until an aerosol of the condensed components is to be generated, that is when the user desires to inhale the aerosol so generated. One embodiment of the method comprises the moving of the container or the source of heat to place the source of heat adjacent the container where a vapor can be generated. In another embodiment, the method comprises a means for energizing a heating source adjacent to the container when the aerosol is to be generated.

The present invention also provides a smoking apparatus to enable the smoking of an aerosol generated from the condensed constituents of tobacco smoke without the harmful gaseous constituents normally carried in tobacco smoke. This apparatus comprises a housing with a container of the condensed constituents of tobacco smoke located within the housing. A heating means is also located to generate a source of heat in relation to the container to thereby generate an aerosol of the condensed constituents which is capable of being inhaled by a smoker. A tube is associated with the housing to receive the generated aerosol and an outlet end is provided on the tube to be engaged by the smoker so as to receive the generated aerosol in the smoker's mouth and respiratory tract.

This invention possesses many other advantages and has other purposes which will be made more clearly apparent from a consideration of the forms in which it may be embodied. They general principles of the invention, but it is to be understood that such detailed descriptions are not to be taken in a limiting sense.

BRIEF DESCRIPTION OF THE DRAWINGS

Figure 7:
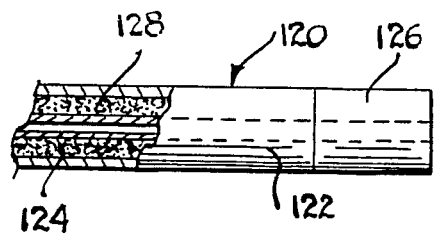
Figure 8:
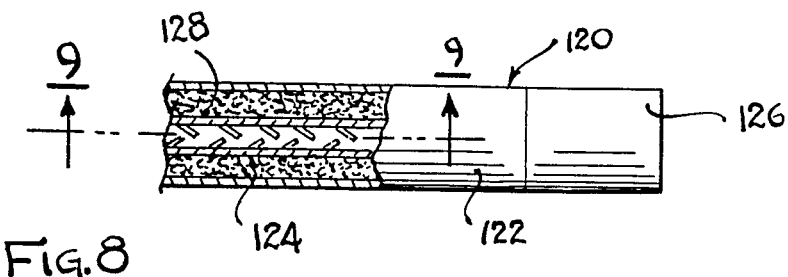
Figure 9:
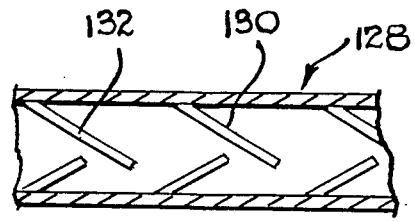
Figure 10:
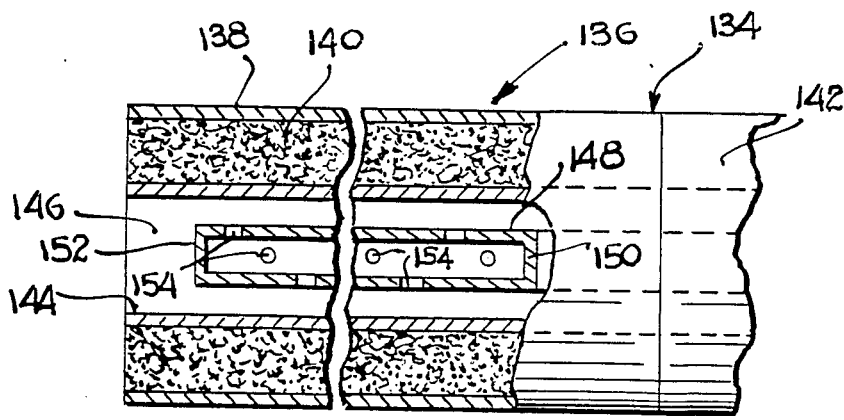
Figure 11:
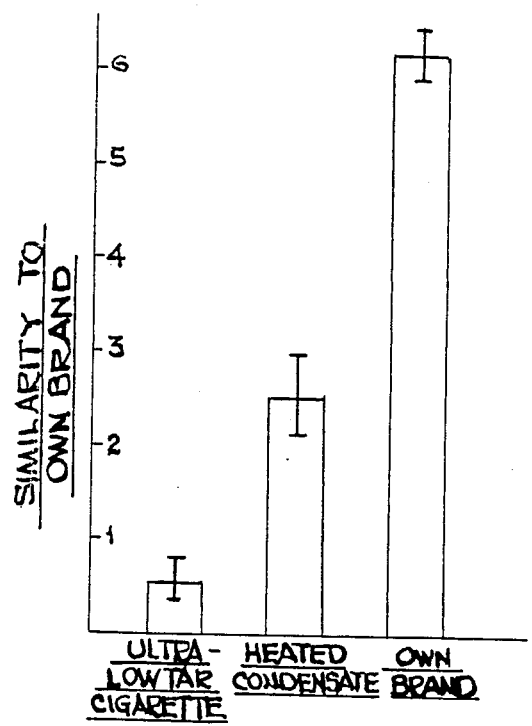
Figure 12:
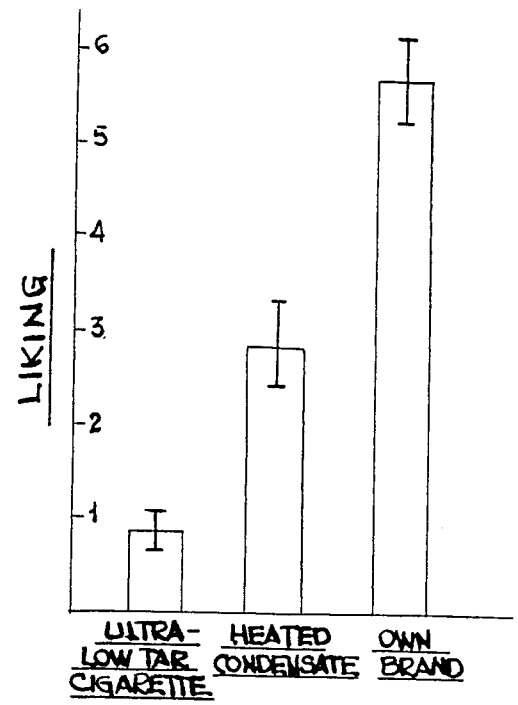
Figure 13:
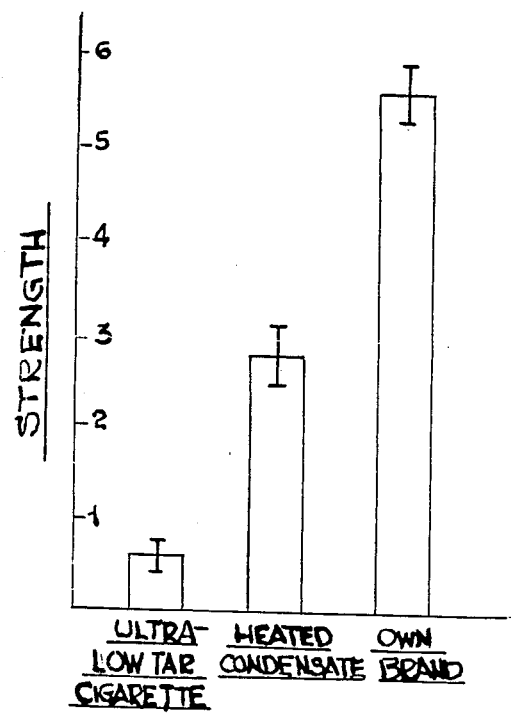
Figure 14:
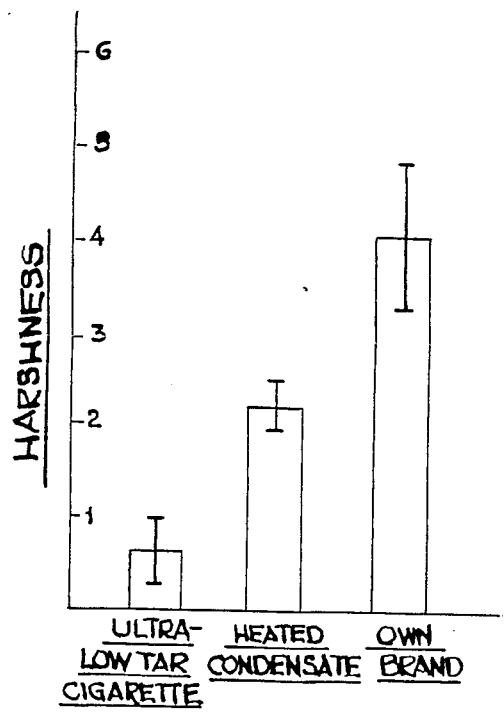

Having thus described the invention in general terms, reference will now be made to the accompanying drawing in which:

FIG. 1 is a schematic side elevational view, partially in section, of an apparatus for generating a tobacco smoke condensate capable of being smoked when in an aerosol form and which is constructed in accordance with and embodies the present invention;

FIG. 2 is a schematic side elevational view, partially in section, of a modified form of apparatus for generating a tobacco smoke condensate capable of being smoked when in an aerosol form;

FIG. 3 is a side elevational view of an apparatus capable of being used for smoking a tobacco smoke condensate upon forming an aerosol thereof;

FIG. 4 is a vertical sectional view of the apparatus of FIG. 3;

FIG. 5 is a side elevational view, partially in section, of a modified form of apparatus for smoking a tobacco smoke condensate and which is also constructed in accordance with and embodies the present invention;

FIG. 6 is a schematic side elevational view, partially in section, of a large scale system for generating tobacco smoke condensate in accordance with the present invention;

FIG. 7 is a schematic side elevational view, partially broken away and in section, and showing another modified form of apparatus for smoking a tobacco smoke condensate and which is also constructed in accordance with and embodies the present invention;

FIG. 8 is a schematic side elevational view, partially broken away and in section and showing another modified form of apparatus for smoking tobacco smoke condensate and which is constructed in accordance with and embodies the present invention;

FIG. 9 is a fragmentary sectional view taken along line 9—9 of FIG. 8;

FIG. 10 is a schematic side elevational view, partially broken away and in section and showing a further modified form of apparatus for smoking a tobacco smoke condensate and which is constructed in accordance with and embodies the present invention;

FIG. 11 is a graph showing a smokers ranking of similarity of smoke from various sources thereof;

FIG. 12 is a graph showing smokers ranking of liking for smoke from various sources thereof;

FIG. 13 is a graph showing smokers ranking of strength of smoke from various sources of smoke; and FIG. 14 is a graph showing smokers ranking of harshness of smoke from various sources thereof.

DETAILED DESCRIPTIONS OF THE PREFERRED EMBODIMENTS

Referring now in more detail and by reference characters to the drawings, FIG. 1 designates an apparatus for collecting tobacco smoke condensate. This apparatus comprises an outer housing 10 with a collection reservoir or container 12 disposed on the lower wall thereof. The upper wall of the housing 10 is provided with an opening 14 to receive an elongate tube 16 such as a Pasteur pipette and which tapers from its upper end to its lower end. The Pasteur pipette has a lower tip portion 18 which terminates either immediately above or in the collection reservoir 12. Finally, the housing 10 is provided with a vacuum port 20 for connection to a suitable vacuum source.

Connected to the upper end of the Pasteur pipette 16 is a receiving tube 22 having an enlarged end 24. This enlarged end 24 is suitably sized and shaped to retain a cigarette 26.

When the cigarette is ignited, a vacuum can be applied to the housing 10 through the vacuum port 20. Inasmuch as the cigarette 26 is in communication with the negative pressure in the housing 10, a continuous draw will be created on the cigarette 26 thereby continuously causing a burning action of the cigarette and pulling smoke generated thereby into the housing 10. Smoke will thereupon travel through the Pasteur pipette 16. Due to the fact that the Pasteur pipette 16 is tapered downwardly, there is an increasing velocity imparted to the smoke stream as it travels downwardly through the Pasteur pipette 16. Toward the tip portion 18, the smoke stream reaches a fairly high velocity.

Immediately after the gaseous constituents exit the lower end of the Pasteur pipette and enter the housing 10, due to the large volume thereof, the smoke will move at a much slower velocity. Since, the tip portion 18 is located within a relatively confined space such that the smoke must change direction at a relatively sharp angle, almost approximating 180 degrees, this causes the condensed constituents in the tobacco smoke to separate from the gaseous constituents. Thus, the condensed constituents will separate and collect in the reservoir 12 permitting the gaseous constituents to travel through the housing 10 and out through the vacuum port 20 where they can be expelled.

The reservoir 12 containing the condensed constituents can then be retained for later smoking of the condensed constituents, as hereinafter described. These condensed constituents form a relatively thick tar-like substance. Nevertheless, when aerosolized, the condensed constituents will form a tobacco smoke very similar to normal tobacco smoke approximating both the taste and the appearance of normal tobacco smoke.

FIG. 2 illustrates another apparatus for collecting the condensates of tobacco smoke and comprises an outer elongate tube 30 having an enlarged head-end 32 for retaining a conventional cigarette 34. The tail-end of the tube is provided with a vacuum port 36 for connection to a suitable vacuum source to impart a draw or suction upon the tube 30. Moreover, located intermediate the ends of the tube 30 is an enlarged section 38 containing a filter 40, such as a Cambridge filter pad, or other filter capable of extracting smoke particulates, but which allows the gaseous constituents to pass therethrough. In effect, the filter pad 40 is placed in a series position with respect to the head-end 32 and the vacuum port 36.

The lower end of the enlarged section 38 serves as a reservoir section 42 for collection of the tobacco smoke condensate. Thus, when a vacuum is imparted to the tube 30, smoke from the cigarette 34 will be pulled through the tube 30. The condensed constituents will be collected by the Cambridge filter pad 40 will collect in the reservoir section 42. The gaseous constituents will be expelled at the vacuum port 36.

FIGS. 3 and 4 illustrate one embodiment of an apparatus for smoking of an aerosol of the tobacco condensate and comprises an outer housing 50 which may adopt the size and shape of a conventional cigarette. For this purpose, the housing 50 is elongate and cylindrically shaped. Located within the housing 50 is a concentrically disposed, diametrically reduced cylindrically shaped divider 54 which forms an ignitable fluid chamber 56 containing a suitable ignitable fluid, such as a conventional lighter fluid e.g. liquid propane, butane, or the like. Any conventional petroleum distillation, such as conventional lighter fluids may be employed for this purpose. Ethanol has been found to be highly effective for this purpose.

A pair of intermediate discs or walls 52 and 53 are located within the housing 50. Concentrically disposed within the divider tube 54 is an elongate smoke delivery tube 58. Mounted on the right-hand end of the smoke delivery tube 58, reference being made to FIGS. 3 and 4 is a filter 60 to create a draw or inhalation resistance, such as in a conventional cigarette filter. Located at the opposite end of the smoke delivery tube 58 is an enlarged ampule or reservoir 62 containing the tobacco smoke condensate. The ampule may be formed of glass or graphite or other inert material.

Extending from the chamber containing the ignitable fluid 56 is a wick 64 having an end 66 capable of being ignited to create a flame. However, by reference to FIGS. 3 and 4, it can be observed that the ampule 62 is located in a position where it is not immediately above the flame of the burnable end 66 and therefore is not heated. When the smoker desires to create an aerosol of the condensed constituents in the ampule 62, the smoke delivery tube 58 and hence the ampule 62 are shifted to the left, reference being made to FIGS. 3 and 4. The condensate in the ampule 62 will become heated and form an aerosol.

The ampule 62 may be provided with an air inlet opening 63 so that when a suction is imparted to the ampule 62, through the smoke delivery tube 58, the aerosol will travel through the smoke delivery tube 58 and through the filter 60. A similar opening 65 may be formed in the end wall of the housing 50 for this purpose. The air inlet opening 63 also operates as a vent to prevent excessive pressure build-up within the ampute 62. Thus, when the smoker desires to inhale an aerosolized amount of the tobacco condensate, he will merely push on the smoke delivery tube 58 so that the ampule 62 is located over the flame of the burnable end 66 and within a matter of a few seconds, a sufficient amount of aerosol has formed, equivalent to that which would be generated in a puff by the smoker on a normal cigarette. The aerosolized condensate which, in effect, forms a regenerated tobacco, is visually identical to normal cigarette smoke and provides a similar aroma and other sensory qualities resembling cigarette smoke.

A spring 68 is disposed between the right-hand end wall 52 in the outer housing 50 and the filter 60. Moreover, an outer cover sleeve 70 is disposed over the spring between the filter 60 and the housing 50. The housing 50, as well as the sleeve 70, may both be formed of a suitable paperboard material which is relatively inexpensive so that the entire apparatus functions as a disposable cigarette which may be disposed of when the charge of condensate in the ampule 62 has been depleted. Otherwise, the entire apparatus FIGS. 3 and 4 could be constructed to be reusable with the ampule capable of being recharged.

One of the distinct advantages of the smoking apparatus of FIG. 3 and 4 is that it can be constructed at a relatively inexpensive cost and is highly effective in producing an aerosol of the tobacco smoke condensate. Moreover, it is only necessary to boil the condensate at a relatively low temperature e.g. about 100 degrees C. As a result, there is no combustion and hence the poisonous products of combustion as for example, in a normal cigarette which is combusted at about 800 degrees C., are avoided. In this respect, carbon monoxide is suspected to be one of the main contributors to coronary artery disease and one of the leading causes of death from cigarette smoking. Thus, there is substantial reduction in the risk associated with smoking despite the fact that the tar and nicotine may be delivered to the smoker.

FIG. 5 illustrates still another embodiment of an apparatus for generating a tobacco smoke aerosol which is capable of being smoked. This embodiment of the apparatus comprises an outer housing in the form of an L-shaped tube 80 and which has a reduced end 82 capable of being engaged by the lips of a smoker. Removably secured to the lower end of the vertical leg of the tube 80 is an ampule or reservoir 84 containing a charge of tobacco smoke condensate 85. A heater section 86 is located immediately beneath the ampule 84 and contains a heating coil 88 which may be energized by means of a battery 90. A switch 92 is electrically connected between the battery and the heating coil 88 to cause energization of the heating coil 88, when actuated. In this way, when the heating coil 88 is energized, it will heat a charge of the tobacco smoke condensate, thereby causing the generation of an aerosol in the tube housing 80.

The tube housing 80 is also provided with an air inlet aperture 94 containing a conventional cigarette filter 96 located therein. The conventional cigarette filter 96 operates in the same manner as a the cigarette filter 60 to create a draw resistance similar to that provided by the filter on a conventional cigarette. Moreover, the filter 96 also serves to preclude the escape of the aerosol through the opening 94. In this way, when the smoker draws on the reduced end 82, the smoker will receive the aerosol of the tobacco smoke condensate, much in the same manner as with the apparatus of FIGS. 3 and 4. It should be recognized that in this embodiment of the invention, the apparatus is a non-disposable apparatus such that the ampule can be removed and recharged.

By using a smoke delivery tube of proper length, as for example, the smoke delivery tube 58 or the tube housing 80, it is possible to obtain a selective fractionation of vaporized condensate. One type of fractionation which is easily achievable in the apparatus of the present invention is a selective distillation of the vaporized condensate. The fraction of the condensate with a higher boiling point will condense first along the length of the smoke delivery tube. The lower boiling point fraction of the condensate which contains a lesser amount of the tar will remain in the aerosol to be inhaled by the user thereof.

Another type of selective fractionation which can be achieved to control the composition of the aerosol utilizes the principles of gas-liquid chromotography. By properly coating the interior surface of the smoke delivery tube, it is possible to selectively absorb certain fractions of the aerosolized condensate. For example, by coating the smoke delivery tube with a paraffin, the components with a high affinity for the paraffin will collect on the wall of the smoke delivery thereby leaving only the other condensate components for delivery to the smoker.

It is also possible to add a selected alcohol to the condensate in order to control the aerosolization thereof. Certain boiling point constituents will preferentially condense on the wall of the smoke delivery tube to thereby control the fraction of the constituents which are delivered to the smoker.

The selective distillation which inherently occurs with a longer length of smoke delivery tube has been found to be highly beneficial in that some of the smokers of the tobacco condensate initially complained of a somewhat "burnt" taste. However, by the selective distillation process, it was found that the undesirable taste was associated with constituents of certain boiling points. Inasmuch as these constituents may deposit along the length of the smoke delivery tube, the sensations and effects achieved by the smoker very closely approximate those achieved with a normal cigarette. Thus, the invention has been found to be highly effective as an alternate source of tobacco smoke without many of the harmful constituents normally found in tobacco smoke.

It is also possible to generate an aerosol without the necessity of heat to boil the condensate. In this case, the condensate could be mixed with a suitable carrier such as ethanol or the like. Generally, about one to about ten percent of the condensate is added to about 90% to about 99%, by weight, of the solvent. Thus, when the carrier and condensate is nebulized, it is possible to generate an aerosol for delivery to the smoker.

Any conventional nebulizer may be used with the solvent carried condensate in order to form the aerosol. Further, the solvent carried condensate may be added to any of those liquid carriers normally employed in aerosol containers. For example, some of the liquid carriers which may be used are the same as those employed in inhalers, as for example, bronchial dilators. The liquid carrier should be relatively inert so that it does not react with the condensate.

It is known that the size of the aerosol particle will affect the portion of the respiratory tract to which the particles are delivered. The smaller sized particles will migrate to the lower respiratory tract and the larger size particles will remain in the oral cavity and in the upper respiratory tract. In addition, it is also known that one of the pleasures achieved by the normal smoker, in addition to taste, is the so-called "scratching sensation" experienced by the smoker when the smoke passes through the respiratory tract. By controlling the size of the aerosol particles, it is also possible to control the areas of the respiratory tract to which the aerosolized condensate may be delivered. By using a particle size within a range of about one micron to about five microns, the aerosol will penetrate to the lower respiratory regions for stimulation of those regions. The larger particles such as droplets in the range of about 5 microns to about ten microns will not penetrate very deeply into the respiratory tract and thus, they will stimulate the higher respiratory tract region. In this way, it is possible to stimulate that portion of the respiratory tract from which the smoker receives the greatest sensation. Normal cigarette smoke particle sizes may be in the range of about 0.2 microns. Thus, by controlling the size of the particles to be at least one micron and larger, only small amounts of the aerosolized condensate, if any at all, will penetrate to the alveoli.

In accordance with the present invention, it is desirable to generate on the average, particles in the size range of about 1 micron to about 10 microns. Preferably, it is desirable to generate aerosol particles having a size within the range of about 2.5 microns to about 8 microns. It is recognized that some particles may be slightly larger than the maximum of these ranges and some may be slightly smaller than the minimum of these ranges although on the average, the particles will be within the specified regions.

Moreover, by using particles in the size of at least 5 microns, a large portion of the aerosolized condensate will settle in the oral cavity. In this way, a substantial concentration of nicotine taste can be obtained with only a very small amount of the condensate. By using a proper mix of the larger sized particles than the smaller sized particles, the latter will penetrate to the lower respiratory tract thereby providing some of the physical stimulation to which the smoker is normally accustomed with conventional cigarette smoke.

The aerosolized condensate particles obtained in accordance with the present invention usually are within the range of about one to ten microns. It is theorized that there are a large number of nuclei present in the combustion of tobacco smoke whereas, in the re-heating, there is a substantially lesser amount of nuclei and hence, the particle sizes are larger. It is possible to control the aerosol particle size by adding solvents of known boiling points.

One important aspect which can be achieved by using the reconstituted smoke of the present invention is the fact that the content of nicotine can be reduced in the condensate, and even completely eliminated. In conventional cigarette smoke, it is virtually impossible to control the amount of nicotine in the smoke, except by processing of the tobacco. In the present invention, it is a relatively easy and simple matter to remove the nicotine. In this way, the smoker could be provided with condensates over a period of time which have progressively lesser amounts of nicotine in order to reduce nicotine dependency.

FIG. 6 illustrates still another embodiment of a commercial scale apparatus for generating tobacco smoke condensate on a large-scale basis. In this embodiment, a tray 100 is provided with tobacco leaves or other form of tobacco or other grown plant substances capable of being burned. A heating source 102 as for example, a conventional gas flame heater is located immediately beneath the tray 100 for causing a burning of the tobacco leaves. A hood 104 is disposed over the tray 102 and delivers the tobacco smoke which is generated from the burning tobacco leaves through a tube 106 into a receiving chamber 108.

A plurality of the Pasteur pipettes 110 are located within the receiving chamber 108 and an individual receptacle 112 is located beneath each of the lower ends of the Pasteur pipettes 110. Larger diameter tubes than the Pastuer pipettes 110 could be employed by merely increasing the velocity of the smoke streams as they pass through the tubes. Finally, the receiving chamber is provided with a discharge pipe 114 connected to a suitable vacuum source for removal of the generated gaseous constituents. When the tobacco smoke passes through the lower end of the each of the individual Pasteur pipettes, the constituents contained within the smoke stream will become deposited within and are collected in the individual reservoirs 112.

FIG. 7 illustrates yet another modified form of an apparatus for smoking a tobacco smoke condensate and which comprises a conventional filter tipped cigarette 120 comprised of a paper tube 122 filled with ground tobacco 124. A conventional filter 126 is provided at the right-hand end of the cigarette in a conventional manner. The present invention provides an elongate tube 128 extending concentrically within the cigarette from one end thereof to the other and which is opened at each of the opposite ends. The tube 128 may also be formed of a paper material or similar burnable substance.

The tube 128 is provided on its interior with a tobacco smoke condensate. In this case, the condensate could be in the form of a heavy tar-like residue which is coated on the interior surface of the tube 128. The burning cigarette 120 will provide the source of heat which will volatilize the condensate. Thus, as the left-hand end of the cigarette is ignited, the heat from the burning end of the cigarette will volatilize the condensate enabling the condensate to be inhaled by the smoker upon puffing at the filter 126.

In accordance with this construction, inasmuch as there is very little draw resistance through the tube 128, approximately 90 per cent of any of the intake by the smoker will be through the tube 128. Any drawing of air through the burning end of the cigarette will indeed produce cigarette smoke, although this will be in a substantial minority. This type of smoking apparatus also may have a great deal of appeal to many smokers, inasmuch as they will be smoking a device which has the appearance and feel of a conventional cigarette and will actually receive un-altered cigarette smoke along with the vaporized tobacco smoke condensate.

It is also possible to use a reconstituted tobacco sheet in place of the conventional ground tobacco 124 and which is processed in order to have less carcinogenic materials. Other techniques for treating the tobacco material 124 could also be employed.

FIGS. 8 and 9 illustrate another modified form of smoking device 120 and which is very similar in construction to the smoking device 120 of FIG. 7 in that it employs a conventional filter tip cigarette. In this embodiment, the elongate smoke delivery tube 128 is provided on its interior surface with a plurality of radially inwardly extending somewhat flexible fingers 130. These fingers may actually adopt the form of filaments and are sufficiently flexible so as to yield to the draw of aerosol through the delivery tube 128. The fingers 130 generally extend randomly throughtout the annular interior surface of the delivery tube 128 and are effective to preclude any of the liquid condensate from rolling out of the delivery tube 128 when the cigarette is held in a vertical position with the outer end located downwardly. Thus, the liquid condensate will collect in the spaces 132 between the point of connection of the fingers 130 and the interior surface of the wall of the tube 128.

FIG. 10 illustrates still a further modified form of an apparatus 134 for smoking a tobacco smoke condensate. This apparatus 134 similarly employs a conventional filter tip cigarette 136 having a paper tube 138 filled with tobacco 140. At its right-hand end, the tube 138 is provided with a conventional cigarette filter 142. The tobacco 140 is confined between the tube 138 and an interior concentrically disposed axially extending retaining tube 144 thereby defining an annularly extending chamber which receives the tobacco 140.

The tube 144 is provided with an interior axially extending chamber 146 to receive a condensate retaining tube 148 which extends concentrically within a portion of the tube 144. The condensate retaining tube 148 is provided with enclosed end walls 150 and 152. Moreover, the condensate retaining tube 148 is provided with a plurality of small apertures 154 around the annular surface thereof.

In accordance with this construction, the condensate retaining tube 148 permits the release of an aerosol which is formed when the cigarette 134 is smoked. The heat will cause an aerosolization of the condensate which then escapes through the various apertures 154 and into the interior chamber 146 of the tube 144. As this occurs, and as the smoker draws upon the cigarette, the smoke will pass along the annular space 146 between the intermediate tube 144 and the condensate retaining tube 148. Moreover, inasmuch as the condensate retaining tube 148 is generally closed except for the openings 154, there is little loss therefrom.

The various components forming part of the smoking apparatus 134 could be formed of a paper or paperboard material much in the same manner as a conventional cigarette to thereby provide the same appearance and same feeling sensations when handled, as a conventional cigarette. Moreover these components will burn along with the tobacco in the same manner as a conventional cigarette. The space between the tube 144 and the condensate retaining tube 148 is sufficient so that the tube 148 will not burn but, will be heated by the burning tobacco. If desired the tube 148 could be formed of a non-burnable plastic material.

The composition of the condensed constituents could be varied by adjusting the temperature thereof. Higher temperatures would deliver more nicotine in view of the fact that nicotine has a relatively high boiling point and hence a lower vapor pressure at a given temperature than many of the other smoke constituents. Thus, if the condensate was subjected to a prolonged heating at a low temperature most of the more volatile components would be vaporized. If the remaining residue of the condensate was placed in a smokers heating apparatus, a higher temperature vaporization thereof would cause smoke of specific constituents and which would be rich in the less volatile components.

It is also possible to add various components to the condensate or residue from the tobacco smoke. For example, nicotine could be added in order to provide for a higher nicotine concentration delivery to the smoker. In like manner, sweetners or other ingredients could be added to the ampule in order to alter the composition of the aerosol which is ultimately delivered to the smoker.

The composition of the condensate can also be altered by using chemical extraction procedures in order to remove known or suspected hazardous substances. Thus, a wide range of smoke compositions could be obtained and which would be free of many of the hazardous gaseous combustion products, and when using the extraction procedures mentioned above, the condensates could be freed of many of the hazardous condensed constituents. As an example, the smoke condensate could be treated with ether and two normal sulfuric acid solutions and then fractionated with sodium bicarbonate and sodium hydroxide solutions. The residue is then fractionated in a silicon gel column and washed with n-hexane to remove a large number of the known carcinogenic substances. This treatment, as well as others which may be employed, are described in Tobacco and Tobacco Smoke, Studies in Expermential Carcinogenesis, by Ernest L. Winder et al, Academic Press, 1967.

It can be observed that one of the significant advantages of the smoking of the regenerated tobacco smoke over current smoking practices is the elimination of the numerous poisonous combustion products normally present in tobacco smoke. The resemblance to conventional smoke coupled with the reduction in risk provide the present invention with a considerable advantage over low tar and nicotine cigarettes.

Another one of the unique aspects of the present invention is that it is possible to control particle size of the aerosol which is formed. By increasing the size of the aerosol particles, it is possible to cause a larger portion of the aerosol to remain in the oral cavity and the upper respiratory tract. By obtaining a reduced aerosol particle size, the aerosol will more freely travel to the lower respiratory tract. By adding a solvent of known boiling point, it is possible to affect the condensation process and also to increase the size of the aerosol particles. Further, and in this way, it is possible to deliver larger size aerosol particles to the oral cavity thereby increasing the taste of nicotine without the actual increase in nicotine concentration.

Another one of the distinct advantages of the smoking apparatus of the present invention is that it effectively eliminates the so-called "side stream" smoke, that is, smoke which is generated by a burning cigarette even when the smoker is not smoking that cigarette. In this case, there is no generation of smoke from the smoking apparatus and the generated smoke is effectively inhaled by the user thereof.

EXAMPLES

The invention is further illustrated by, but not limited to the following examples.

EXAMPLE 1

A liquid condensate was generated in accordance with the present invention by using Pall Mall non-filter cigarettes. A number of the Pall Mall cigarettes were connected to an apparatus of the type illustrated in FIG. 1 using a Pasteur Pipette. After sufficient amount of vacuum was applied, a large amount of the condensate was generated in the ampule included in the housing of the apparatus and collected. This condensate was then stored for later use in testing of several subjects.

EXAMPLE 2

A test of eight smokers was made in order to compare several qualities of the smoking of regenerated smoke in accordance with the present invention compared to their customary brand of cigarette and compared to an ultra low tar and nicotine cigarette. In this example, a Carlton hard pack cigarette was selected as the ultra low tar and nicotine cigarette.

The heated condensate which was collected, as in accordance with Example 1, was introduced into a smoking apparatus of the type illustrated in FIG. 3. The smoking apparatus was connected to a mouth piece protruding from a divider such that the subjects could not observe the source of generated smoke. A second mouthpiece protruded from the divider and was provided at its opposite end with the low tar and nicotine cigarette and the opposite end of a third mouthpiece was provided with the subjects preferred cigarette brand. Each subject compared a puff from the aerosol with a puff from the low tar and nicotine cigarette and compared that to a puff from his or her own preferred cigarette brand in random sequences and without knowing the source of the inhaled smoke. The three different types of puffs were ranked for similarity to their own brand, a liking, strength and harshness.

The analysis for four different tests is shown in the accompanying FIGS. 11 through 14 in which the smokers ranked the selected source of smoke for similarity to their own preferred brand as in FIG. 11. The smokers ranked the liking for each of the three sources of smoke in FIG. 12 and the strength for each of the three sources in FIG. 13 and finally, the harshness for each of the three sources in FIG. 14.

The statistical analysis of the means and standard deviations indicate that the subjects rated the heated condensate much more similar to their own brand than they did with the low tar and nicotine cigarette. In general, the ratings for similarity to their own brand, liking, strength and harshness were generally similar for the ultra low tar and nicotine cigarette and were similar for the heated condensate aerosol and also similar with respect to their own brands. While the heated condensate aerosol did not rank as high as their own preferred brand, it still ranked sufficiently high to constitute a persuasive alternative to their own cigarette brand, recognizing the reduced hazards associated with smoking the heated condensate aerosol.

EXAMPLE 3

About one gram of condensate produced in accordance with the procedure of Example 1 was mixed with about fifteen grams of ethanol. The condensate is generally soluable in the ethanol and is then tested for use. The condensate produced by Example 1 and mixed with the ethanol was then nebulized with an ultrasonic nebulizer. The sensory effects very closely resembled those of conventional cigarette smoke.

EXAMPLE 4

A liquid condensate was generated in accordance with the present invention by using Pall Mall non-filter cigarettes. A number of the Pall Mall cigarettes were connected to an apparatus of the type illustrated in FIG. 2 using a Cambridge filter pad. After sufficient amount of vacuum was applied, a large amount of the condensate was generated in the trap forming part of the apparatus and collected. This condensate was then stored for later use in testing of several subjects.

Thus, there has been illustrated and described a unique and novel method and apparatus which enables the smoking of a tobacco smoke condensate and which provides most of the normal sensory effects achieved with normal tobacco smoke but which also eliminates many of the hazardous constituents. The present invention thereby fulfills all of the objects and advantages which have been sought. It should be understood that many changes, modifications, variations and other uses and applications will become apparent to those skilled in the art after considering this specification and the accompanying drawings. Therefore, any and all such changes, modifications, variations and other uses and applications which may become apparent to those skilled in the art after considering this specification are deemed to be covered by the invention.

Having thus described my invention, what I desire to claim and secure by letters patent is:

1. A method for producing a tobacco smoke condensate capable of being smoked, said method comprising:
   (a) heating tobacco to produce a tobacco smoke comprised of a mixture of fluidized components and gaseous components,
   (b) separating the gaseous components from the fluidized components,
   (c) expelling the separated gaseous components,
   (d) collecting the fluidized components as a condensate when the gaseous components have been expelled so that an aerosol may be formed therefrom, and
   (e) forming an aerosol with the fluidized components for smoking thereof.

2. The method of claim 1 further characterized in that the step of separating the gaseous components comprises passing a substantial portion of the gaseous components through a filter and causing a trapping of the fluidized components and collection thereof as a condensate in a container.

3. The method of claim 1 further characterized in that the step of separating the gaseous components comprises passing the mixture of gaseous components and fluidized components through a tube sized and shaped to cause a substantial increase in velocity and thereafter causing the mixture to change direction at a relatively sharp angle thereby causing the fluidized components to separate out as a precipitate from the gaseous components.

4. The method of claim 3 further characterized in that the method comprises passing the mixture of gaseous components and fluidized components through a Pasteur pipette to cause the substantial increase in velocity.

5. The method of claim 1 further characterized in that the step of burning tobacco comprises the combustion of tobacco in a cigarette and applying a vacuum to the cigarette to extract the smoke generated thereby.

6. The method of claim 1 further characterized in that said step of burning the tobacco comprises causing combustion of tobacco leaves and drawing smoke generated thereby into a further processing chamber.

7. The method of claim 1 further characterized in that the step of heating comprises rapidly burning the tobacco.

8. An apparatus for producing a tobacco smoke condensate capable of being smoked upon generating an aerosol thereof on a production basis, said apparatus comprising:
   (a) tobacco receiving means for receiving a source of tobacco capable of being rapidly combusted and enabling combustion of the tobacco to produce tobacco smoke,
   (b) a chamber located in proximate relation to the tobacco receiving means for receiving and temporarily holding the tobacco smoke,
   (c) separating means operatively connected to said chamber to receive the tobacco smoke and enable a fractionation of certain constituents to thereby separate the gaseous constituents from the condensed constituents in the smoke, said separating means comprising a filter pad formed of a material and having a pore size such that a substantial portion of the condensed constituents will engage the filter pad material which causes a separation of the condensed constituents to enable collection thereof and which gaseous constituents will pass therethrough,
   (d) exhaust means operatively associated with said separating means to permit discharge of the gaseous constituents, and
   (e) container means operatively associated with said separating means for collecting the condensed constituents as a somewhat liquid condensate which is capable of being easily aerosolized for smoking upon aerosolization thereof.

9. The apparatus of claim 7 further characterized in that the exhaust means comprises a vacuum port downstream of the separating means for connection to a source of a vacuum to thereby create a vacuum to remove the gaseous constituents.

10. The apparatus of claim 7 further characterized in that the tobacco receiving means for receiving the tobacco comprises a tube to hold a cigarette.

11. The apparatus of claim 7 further characterized in that the tobacco receiving means for receiving the tobacco comprises a tray receiving tobacco for combustion therein and which tray is sized to receive a large charge of the tobacco.

12. A method for smoking an aerosol of condensed tobacco smoke constituents to provide the sensory effects of normal tobacco smoke without many of the harmful gaseous constituents therein, said method comprising:
   (a) disposing a container of condensed tobacco smoke constituents separated from tobacco smoke and locating the condensed constituents in a position where they may be contacted by a relatively inert gas from a source of a relatively inert gas, (b) contacting the condensed constituents with the relatively inert gas, (c) generating an aerosol of the condensed tobacco smoke constituents in the relatively inert gas and which aerosol will have an appearance and taste similar to that of normal tobacco smoke, and (d) permitting the aerosol of the condensed constituents to pass through a smoke delivery tube upon drawing by a smoker to allow receipt of the aerosol by the smoker.

13. The method of claim 12 further characterized in that the aerosol is generated by heating the condensed constituents.

14. The method of claim 13 further characterized in that the method comprises locating the container in a position where it is heated in the presence of the inert gas to aid in the generation of an aerosol of the condensed constituents.

15. The method of claim 14 further characterized in that the method comprises moving the container or the source of heat so that the source of heat is disposed in heating relationship to the container to aid in the generation of an aerosol.

16. The method of claim 14 further characterized in that the method comprises energizing an electrical heating source adjacent to the container to aid in the generation of an aerosol.

17. The method of claim 14 further characterized in that the method comprises drawing the aerosol through the smoke delivery tube when the smoker creates a suction on the smoke delivery tube.

18. The method of claim 12 further characterized in that the method comprises selectively distilling the aerosolized condensate into a plurality of fractions such that only certain of said fractions are received by the smoker.

19. The method of claim 13 further characterized in that the step of generating an aerosol comprises nebulizing the condensed tobacco smoke with a stream of inert gas.

20. A smoking apparatus to enable smoking of an aerosol of condensed tobacco smoke constituents without the harmful gaseous constituents normally carried in tobacco smoke, said apparatus comprising:

(a) a housing, (b) a container of condensed tobacco smoke constituents located within said housing, (c) aerosol generating means to generate an aerosol of the condensed constituents which is similar to normal tobacco smoke in taste and appearance and which is capable of being inhaled by a smoker, (d) a tube associated with said housing to receive the generated aerosol, and (e) an outlet end associated with said tube and sized so that a smoker may impart a suction to the tube to receive the generated aerosol.

21. The apparatus of claim 20 further characterized in that the aerosol generating means comprises a heating means to generate a source of heat in relation to the container to thereby cause an aerosol of the condensed constituents.

22. The apparatus of claim 21 further characterized in that a filter is associated with said air inlet opening to increase draw resistance.

23. The apparatus of claim 20 further characterized in that an air inlet opening is formed in said housing to enable introduction of air to form the aerosol and to enable drawing of the aerosol through the housing upon applying suction to the tube.

24. The apparatus of claim 20 further characterized in that said tube has a length sufficient so that selective distillation of the aerosolized condensed constituents will take place therein.

25. A smoking apparatus to enable smoking of an aerosol of condensed tobacco smoke constituents comprising:

(a) an elongate tube, (b) a source of tobacco smoke condensate associated with said elongate tube, and (c) means to generate heat adjacent said source of condensate to generate an aerosol of the condensate without any appreciable combustion of the condensate and which does not contain any appreciable amount of the harmful gaseous constituents in normal tobacco smoke but is similar to normal tobacco smoke in taste and appearance and which is capable of being drawn through said elongate tube and inhaled by a smoker.

26. The smoking apparatus of claim 25 further characterized in that said tube is disposed in a conventional cigarette having a roll of tobacco enclosed within an outer burnable material such that the tube is disposed axially within the roll of tobacco, and that the condensate is located in said tube, and the means to generate heat is the burnable tobacco of said roll disposed around said tube.

27. The smoking apparatus of claim 25 further characterized in that said source of tobacco smoke condensate is formed by previously heating tobacco externally of the tube and the condensate is thereafter associated with the elongate tube.

28. A method of enabling smoking of an aerosol of tobacco smoke condensate to receive the sensory effects of normal tobacco smoke without the harmful gaseous constituents normally present in tobacco smoke, said method comprising:

(a) burning tobacco to produce a mixture of condensed constituents and gaseous constituents, (b) separating and collecting the condensed constituents, and (c) generating an aerosol of the condensed constituents in the smoking device without any appreciable combustion of the condensate to provide a smoke stream which does not contain any appreciable amount of the harmful gaseous constituents in normal tobacco smoke but which is similar in appearance and taste to normal tobacco smoke so that the aerosol can be inhaled by a user thereof with substantially reduced health risk.

29. The method of claim 28 further characterized in that the step of separating and collecting the condensed constituents comprises expelling and discarding the gaseous constituents.

30. The method of claim 28 further characterized in that the method comprises the drawing of the aerosol into a smoke delivery tube upon a smoker applying a suction to the delivery tube.

31. The method of claim 28 further characterized in that the method comprises generating the aerosol by selectively heating the condensate only when the smoker desires to draw the aerosol which is generated.

32. The method of claim 28 further characterized in that the method comprises selectively fractioning the condensed constituents into a plurality of fractions without combustion such that only certain of said fractions are received by the smoker.

33. The method of claim 32 further characterized in that the selective fractioning comprises selectively distilling.

34. The method of claim 28 further characterized in that said method comprises introducing the collected condensed constituents into a container associated with a smoking device after the separating and collection thereof.

35. A method for smoking an aerosol of condensed tobacco smoke constituents to provide the sensory effects of normal tobacco smoke without many of the harmful gaseous constituents wherein, said method comprising:
(a) disposing a container of condensed tobacco smoke constituents separated from tobacco smoke and locating the condensed constituents in a position where they may be contacted by a relatively inert gas from a source of a relatively inert gas,
(b) contacting the condensed constituents with the relatively inert gas,
(c) generating an aerosol of the condensed tobacco smoke constituents having a size on the average within the range of about 2.5 microns to about 10 microns, and
(d) permitting the aerosol to be inhaled by the smoker.

36. The method of claim 35 further characterized in that the aerosol is generated by heating the condensed constituents.

37. An apparatus for producing a tobacco smoke condensate capable of being smoked upon generating an aerosol thereof, said apparatus comprising:
(a) tobacco receiving means for receiving a source of tobacco capable of being combusted and enabling combustion of the tobacco to produce tobacco smoke,
(b) a chamber located in proximate relation to the tobacco receiving means for receiving and temporarily holding the tobacco smoke,
(c) separating means operatively connected to said chamber to receive the tobacco smoke and enable a condensation of certain constituents to thereby separate the gaseous constituents from the condensed constituents in the smoke, said separating means comprising a tube having a reduced diameter section to cause an increase in the velocity of the mixture of gaseous constituents and condensed constituents, said tube forming part of a flow path which causes the mixture to change direction at a relatively sharp angle greater than 90 degrees thereby separating the condensed constituents from the gaseous constituents
(d) exhaust means operatively associated with said separating means to permit discharge of the gaseous constituents, and
(e) container means operatively associated with said separating means for collecting the condensed constituents as a somewhat liquid condensate for smoking upon aerosolization thereof.

38. An apparatus for producing a tobacco smoke condensate capable of being smoked upon generating an aerosol thereof on a production basis, said apparatus comprising:
(a) tobacco receiving means for receiving a source of tobacco capable of being rapidly heated to volatilize tobacco constituents and cause a vapor thereof,
(b) means for heating the tobacco to a temperature sufficient to volatilize tobacco constituents and cause a vapor thereof,
(c) a chamber located in proximate relation to the tobacco receiving means for receiving and temporarily holding the tobacco vapors,
(d) separating means operatively associated with said chamber to receive the tobacco vapor and enable a separation of certain of the volatile constituents from the less volatile constituents while in the heated state,
(e) exhaust means operatively associated with said separating means to permit discharge of the gaseous constituents, and
(f) container means operatively associated with said separating means for collecting the condensed constituents as a somewhat liquid condensate which is capable of being easily aerosolized for smoking upon aerosolization thereof.

39. The apparatus of claim 38 further characterized in that the exahust means comprises a vacuum port downstream of the separating means for connection to a source of a vacuum to thereby create a vacuum to remove the volatile constituents.

40. A method for smoking an aerosol of condensed tobacco smoke constituents to provide the sensory effects of normal tobacco smoke without many of the harmful gaseous constituents therein, said method comprising:
(a) disposing a container of condensed tobacco smoke, constituents separated from tobacco smoke in an environment where the smoke constituents may be vaporized,
(b) generating a vapor of the condensed tobacco smoke constituents in a realtively inert gas,
(c) permitting the vapor of the condensed constituents to pass through a smoke delivery tube upon drawing by a smoker,
(d) causing a selective adsorption of certain of the constituents while moving in a smoke delivery tube so that certain of the constituents in the vapor will again adhere to the tube to thereby further eliminate certain of the constituents from the original tobacco smoke, and
(e) forming an aerosol of the vapor constituents which did not adhere to the tube and which aerosol will have an appearance and taste similar to that of normal tobacco smoke.

41. The method of claim 40 further characterized in that the vapor is generated by heating the condensed constituents.

42. The method of claim 40 further characterized in that said step of selective absorption is selective distillation.

43. A method of enabling smoking of an aerosol of tobacco smoke condensate to receive the sensory effects of normal tobacco smoke without the harmful gaseous constituents normally present in tobacco smoke, said method comprising:
(a) burning tobacco to produce a mixture of condensed constituents and gaseous constituents,
(b) separating and collecting the condensed constituents, and
(c) selectively heating and generating an aerosol of the condensed constituents only when the smoker desires to draw an aerosol and thereby to provide a smoke stream similar in appearance and taste to normal tobacco smoke so that the aerosol can be inhaled by a user thereof.

* * * * *